US009651530B2

(12) United States Patent
Blomberg et al.

(10) Patent No.: US 9,651,530 B2
(45) Date of Patent: May 16, 2017

(54) METHODS AND APPARATUS FOR MEASURING NITRIC OXIDE IN FLUID

(71) Applicant: LIFEHEALTH, LLC, Charlotte, NC (US)

(72) Inventors: Scott Everett Blomberg, Plymouth, MN (US); Mark Louis Peterson, Chanhassen, MN (US); Amanda Marie Franey, Princeton, MN (US); Jonathan S. Stamler, Roseville, MN (US)

(73) Assignee: LifeHealth, LLC, Roseville, MN (US)

( * ) Notice: Subject to any disclaimer, the term of this patent is extended or adjusted under 35 U.S.C. 154(b) by 782 days.

(21) Appl. No.: 13/843,562

(22) Filed: Mar. 15, 2013

(65) Prior Publication Data

US 2014/0197043 A1    Jul. 17, 2014

Related U.S. Application Data

(60) Provisional application No. 61/752,435, filed on Jan. 14, 2013.

(51) Int. Cl.
*G01N 27/416* (2006.01)
*G01N 33/00* (2006.01)

(52) U.S. Cl.
CPC ..... *G01N 33/0011* (2013.01); *G01N 33/0037* (2013.01)

(58) Field of Classification Search
CPC ...... G01N 27/28; G01N 27/416; A61B 5/412; A61B 5/14546
See application file for complete search history.

(56) References Cited

U.S. PATENT DOCUMENTS

| 5,459,076 A | 10/1995 | Stamler et al. |
|---|---|---|
| 2011/0008815 A1 | 1/2011 | Stamler et al. |
| 2014/0127081 A1* | 5/2014 | Fine ........ C01B 21/24 422/119 |

FOREIGN PATENT DOCUMENTS

CN    105247340 A    1/2016

OTHER PUBLICATIONS

"U.S. Appl. No. 14/155,346, Non Final Office Action mailed Feb. 26, 2016", 19 pgs.
"U.S. Appl. No. 14/155,346, Response filed Nov. 12, 2015 to Non Final Office Action mailed Aug. 12, 2015", 9 pgs.
"U.S. Appl. No. 14/155,346, Non Final Office Action mailed Oct. 7, 2016", 12 pgs.
"U.S. Appl. No. 14/155,346, Preliminary Amendment filed Mar. 28, 2014", 5 pgs.
"U.S. Appl. No. 14/155,346, Response filed Jun. 27, 2016 to Non Final Office Action mailed Feb. 26, 2016", 10 pgs.

(Continued)

*Primary Examiner* — Gurpreet Kaur
(74) *Attorney, Agent, or Firm* — Schwegman Lundberg & Woessner, P.A.

(57) ABSTRACT

An exemplary apparatus for measuring nitric oxide in a fluid includes a sample injection port; a pump and reservoir; a valve; a measurement chamber; an electromagnetic radiation source; controls and user interface; and a cartridge. The cartridge includes a sample chamber a mix chamber; a sample degassing chamber; and a planar reaction chamber. The cartridge preferably is single-use and disposable. Furthermore, additional inventive aspects and features are disclosed related to measuring nitric oxide in a fluid.

18 Claims, 5 Drawing Sheets

(56) References Cited

OTHER PUBLICATIONS

"Chinese Application Serial No. 201480015156.5, Voluntary Amendment filed Apr. 26, 2016", 6 pgs.
"U.S. Appl. No. 14/155,346, Response filed Jan. 6, 2017 to Non Final Office Action mailed Oct. 7, 2016", 9 pgs.
"Chinese Application Serial No. 201480015156.5, Office Action mailed Jan. 13, 2017", W/ English Translation, 19 pgs.

* cited by examiner

METHODS AND APPARATUS FOR MEASURING NITRIC OXIDE IN FLUID

CROSS-REFERENCE TO RELATED APPLICATION

The present application is a U.S. nonprovisional patent application of, and claims priority under 35 U.S.C. §119(e) to, U.S. provisional patent application Ser. No. 61/752,435, filed Jan. 14, 2013.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

As a preliminary matter, a method is known for measurement of nitric oxide (NO) concentration in a blood sample by (1) introducing the blood sample to a chamber which is transparent to electromagnetic radiation on one side and porous on the other side to allow for NO gas to pass but preventing protein to pass; (2) directing low power electromagnetic radiation to liberate the NO gas molecule from various bound molecules; (3) providing a solvent zone to dissolve liberated NO gas; and (4) measuring liberated NO molecules using an electrochemical method. The low power electromagnetic radiation is provided by a laser or LED. Such a conventional method is disclosed in U.S. Patent Application Publication No. 2011/0008815, which is incorporated by reference herein.

SUMMARY OF THE INVENTION

The present invention generally relates to methods and apparatus for measuring nitric oxide in fluid, and the present invention includes many aspects and features, which are disclosed herein.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
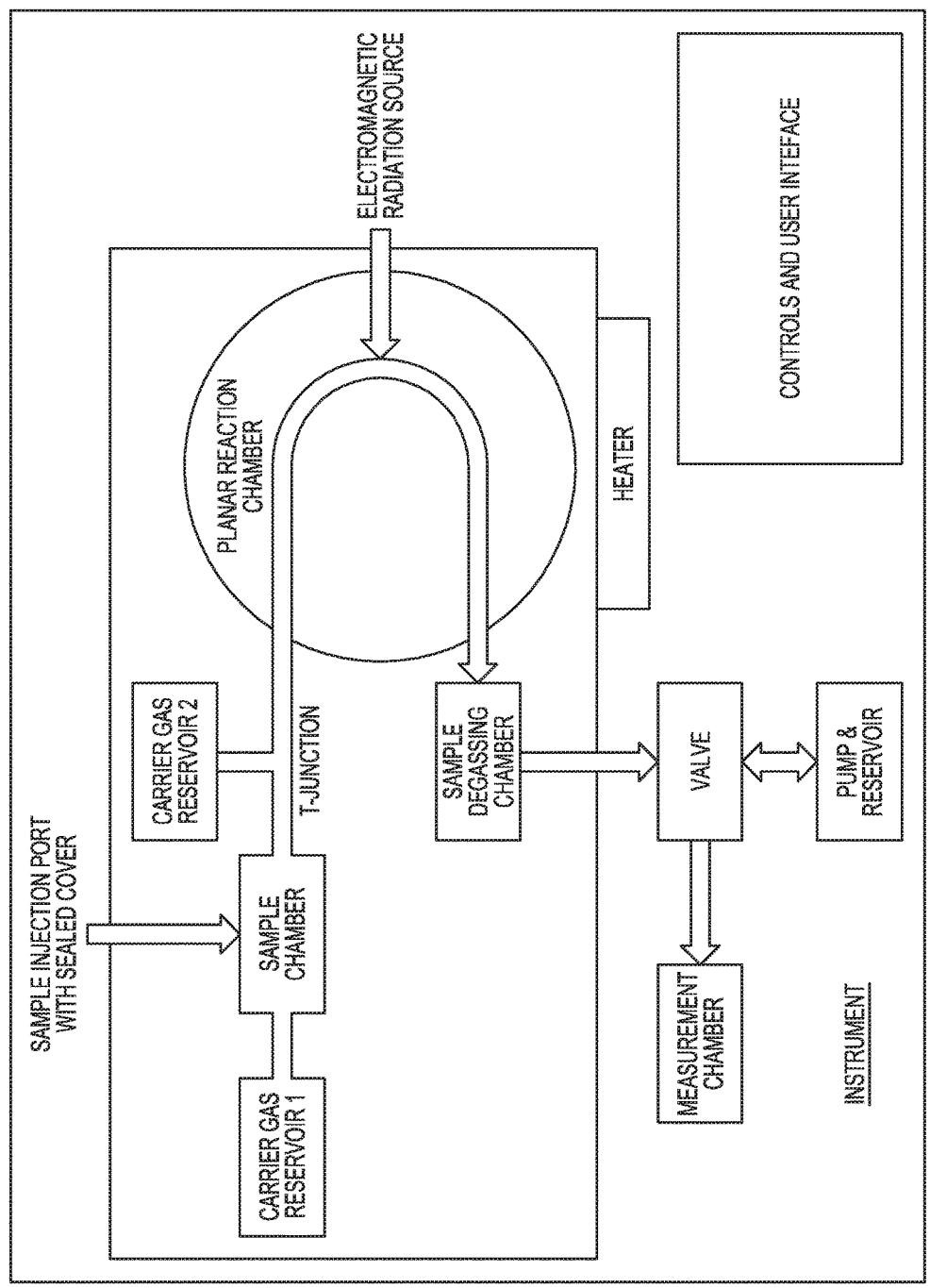
FIG. 1 illustrates a system block diagram.

In accordance with one or more preferred embodiments of the present invention, which are now described in detail with reference to the system block diagram of FIG. 1, a Sample Injection Port (simple luer or needle safe port) is provided for injecting blood or other fluid containing Nitric Oxide into a sample chamber for containing the fluid sample prior to analysis. The Sample Injection Port includes a sealed cover containing the sample in the disposable after injection. The sample chamber is an enclosure into which fluid is stored after being injected into the Sample Injection Port. Two carrier gas reservoirs are provided (Carrier Gas Reservoir 1 and Carrier Gas Reservoir 2). After the cover on the Sample Injection Port is closed and sealed, the Sample Chamber is only connected to Carrier Gas Reservoir 1 on one side and a T-Junction on the other side. The T-Junction is also connected to Carrier Gas Reservoir 2. Both carrier gas reservoirs are approximately the same volume (0.1 ml to 1 ml), contain room air carrier gas and are sealed from outside air. This arrangement allows for the fluid sample to mix with gas from Carrier Gas Chamber 2 simply by pulling the sample through the T-Junction with negative pressure. The size of the individual mixed fluid droplets can be adjusted by adjusting the relative volume of the two carrier gas chambers.

The sample mixture is directed into a planar reaction chamber with at least one surface highly transparent to electromagnetic radiation. While the sample mixture is within this chamber, it is exposed to the radiation and heated thus driving the desired chemical reaction which liberates nitric oxide from the blood.

The disposable cartridge includes a sample degassing chamber. This chamber removes the dissolved NO gas from the fluid sample and keeps all fluid and non-gaseous components of the fluid inside the cartridge. The chamber may comprise a heated surface which drives the outgassing of the fluid through heat vaporization. The chamber may also include a simple gravity mechanism whereby the fluid/gas mixture enters at the bottom and only gas is pumped out at the top leaving fluid and solids behind by the force of gravity. An alternative chamber design includes a gas-permeable hydrophobic membrane which allows for the gaseous components of the fluid/gas mixture to pass and prohibits the passage of fluid. Preferred embodiments include both heat vaporization and a membrane, which acts as a secondary containment mechanism for the fluid and solids left behind after degassing.

The design and construction of the disposable cartridge is such that it can be inexpensively manufactured using common materials such as polymers and manufacturing methods such as molding, thermoforming, extruding and stamping.

With greater regard to the instrument, it contains a programmable pump and valve for the control of gas into and out of the disposable cartridge and into the measurement chamber where the NO gas is measured. The instrument also contains the electromagnetic radiation source, such as a mercury high pressure bulb, metal halide bulb, lasers, LED's or laser diodes, emitting a radiation primarily in the 325-450 nm wavelength range and/or secondarily in the 290-325 nm wavelength range and/or in the 450-600 nm wavelength range. Preferred embodiments comprise LEDs, as LEDs are believed to be smaller, less expensive, draw less power, and generate less heat than the other radiation sources. In addition, the instrument includes microprocessor controller(s) for automated operation, a user interface, and data memory/communication capabilities.

The instrument also includes a sample measurement chamber for measuring nitric oxide gas and quantifying its concentration. In preferred embodiments, the sample measurement chamber is connected to an amperometric electrochemical nitric oxide gas sensor. The sample gas, which includes the nitric oxide and carrier gas, enters the sample measurement chamber and diffuses into the electrochemical sensor. The electrochemical sensor has been optimized for the concentrations in the range of 2 parts per billion (ppb) to 5 parts per million (ppm). The sample measurement chamber is 0.1 to 0.5 milliliter in volume. Alternative methods for measuring nitric oxide include chemiluminescence and spectroscopic fluorescence. For these alternatives, the sample measurement chamber would be design as appropriate for those methods.

With the exception of the sample measurement chamber, the entire system preferably is sealed from the outside environment once the disposable cartridge is inserted into the instrument. It is believed that this is an important feature to controlling the amount of carrier gas within which the NO gas sample is measured. The fluid/gas sample is moved throughout the system by varying the relative pressure of the gas throughout the system using the pump and reservoir.

Figure 2:
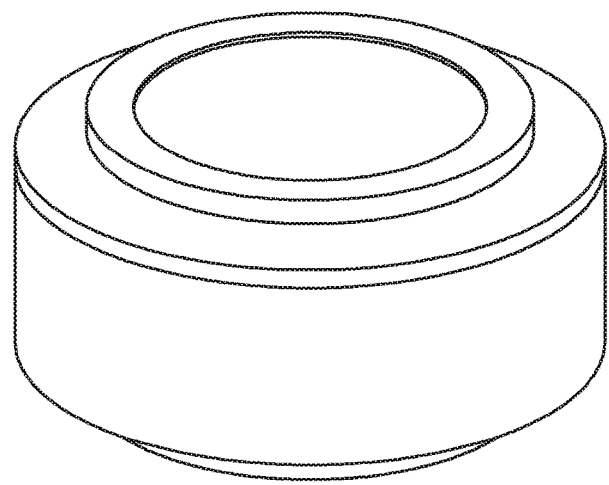
FIG. 2 illustrates a commercially available electrochemical nitric oxide sensor.
Figure 3:
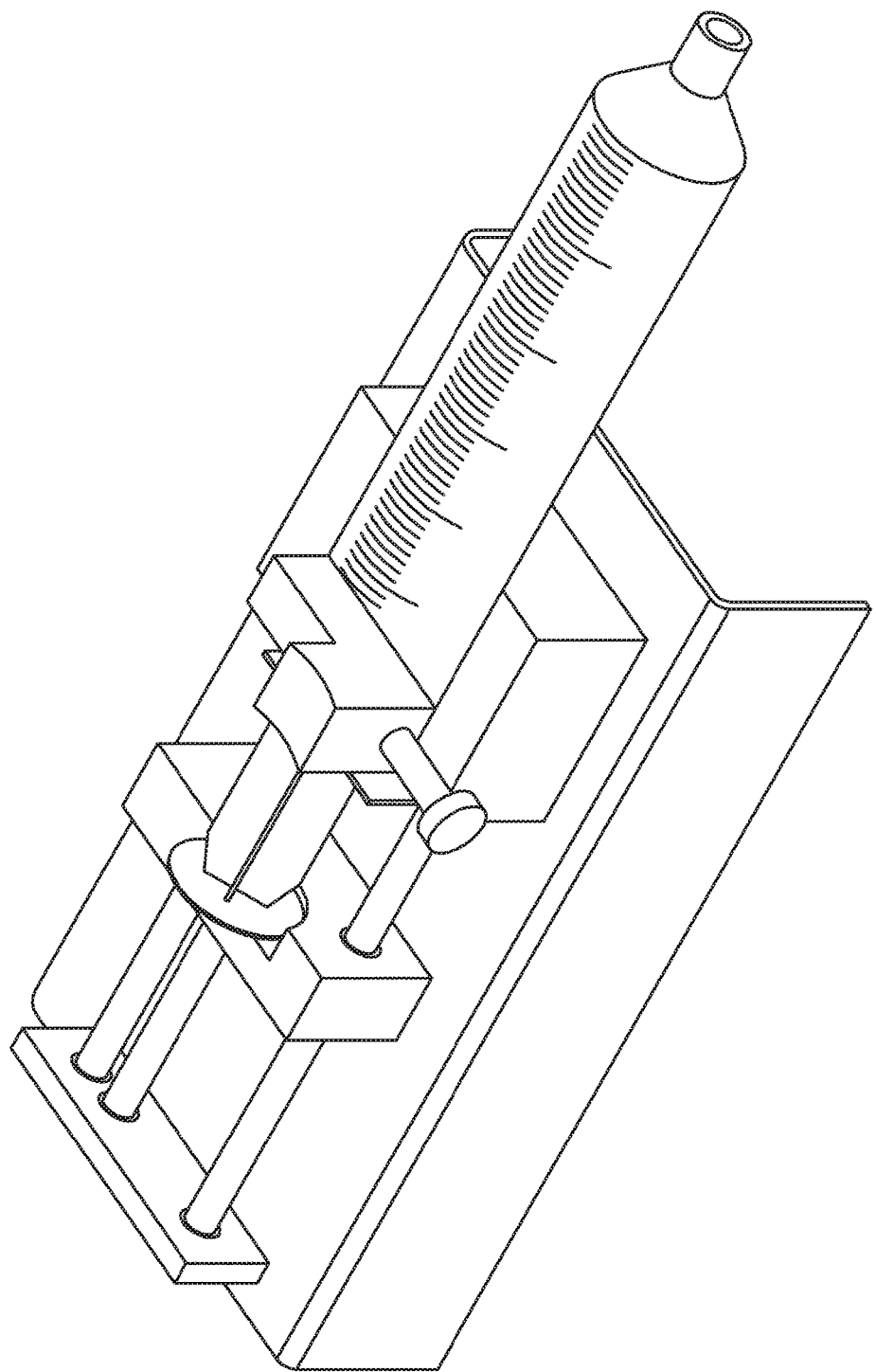
FIG. 3 illustrates a commercially available syringe pump.
Figure 4:
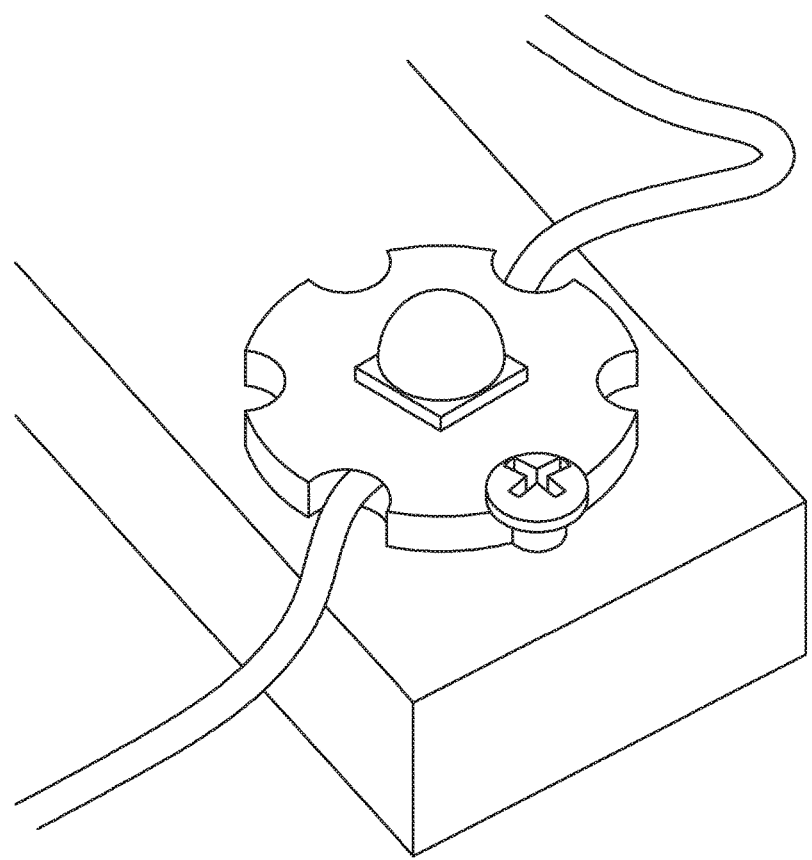
FIG. 4 illustrates a commercially available radiation source.
Figure 5:
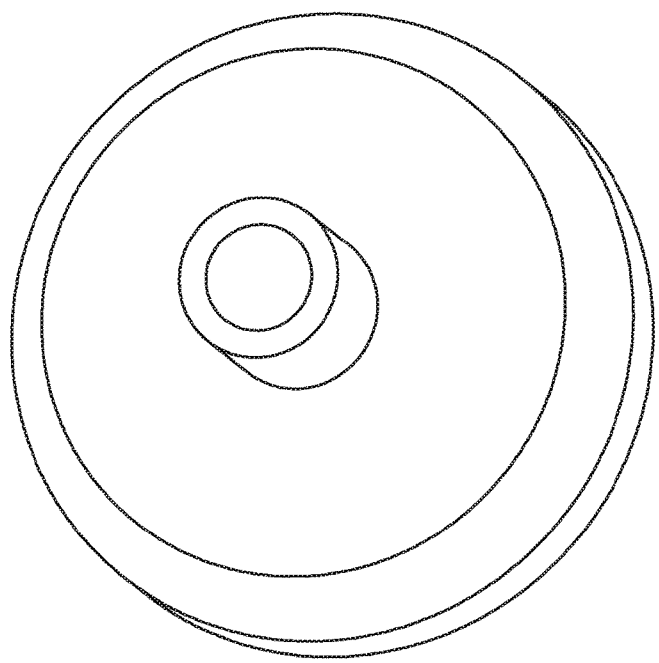
FIG. 5 illustrates a commercially available syringe filter.

FIG. 2 is an illustration of a commercially available electrochemical nitric oxide sensor from Alphasense, Great Notley, Essex, United Kingdom; FIG. 3 is a commercially available syringe pump from New Era Pump Systems, Inc. Farmingdale, N.Y., US; and FIG. 4 is an illustration of a commercially available radiation source having 365 nm UV light emitting diodes (LEDs) available from LED Engin, Inc., San Jose, Calif., US.

With respect to operation of preferred embodiment, the disposable cartridge is inserted into the instrument and the user is asked to inject the sample, typically 25 to 100 microliters into the sample injection port (thus directing the liquid sample into the Sample Chamber), close its sealed cover and select start. Operation after that is fully automated and includes the following steps:

The instrument's Pump (syringe or positive displacement) pulls gas out of system thereby reducing the pressure in the Photolysis Chamber, typically to 100 to 500 millibars. The exhausted carrier gas is stored in a reservoir or alternatively exhausted to reduce total amount of system gas and lower relative system pressure.

The pump continues to pull gas out of the system which causes the sample fluid to move toward the Photolysis Chamber automatically mixing with gas from Carrier Gas Reservoir 2 at the T-Junction creating a liquid/gas mixture. After passing through the T-Junction the liquid/gas mixture enters the Planar Reaction Chamber.

In the Planar Reaction Chamber the sample is exposed to the Electromagnetic Radiation resulting in a chemical reaction. The resulting chemical reaction is nitric oxide (NO) liberated from its bonds to other molecules and becoming a dissolved gas in the fluid. Some NO is immediately degassed out of the fluid via diffusion.

The liquid/gas mixture is then pumped into the Degassing Chamber by the pump thus continuing to reduce pressure through the system.

While passing through the Degassing Chamber, NO is released from the fluid sample by one of the methods described. In the preferred method, the fluid is heated to vaporization outgassing the NO.

The Pump continues to withdraw the majority of the photolysis gas mix into the Pump and Reservoir Chamber.

The instrument's valve is closed sealing the pump and reservoir from the rest of the system. The Pump returns pressure of the gas mix to atmospheric pressure which is optimal for the electrochemical gas sensor.

The valve is opened to the sensor and the Pump directs the photolysis gas mix into the sensor chamber. The sensor measures sample NO in gas form as a fractional percentage of the entire gas sample including the carrier gas. The concentration of the gas is in the range of 2 parts per billion (ppb) to 5 parts per million (ppm). These concentrations correlate to the initial concentration of the bound nitric oxide in the fluid sample. These concentrations are in the range of 10 nanomolar (nM) to 10 micromolar (M). With respect to contemplated alternatives to the foregoing, the Photolysis Chamber may be one of several shapes provided that a sufficient amount of electromagnetic radiation is imparted on the sample during the measurement. These shapes could include a zigzagging maze, a multilevel spiral or a planar spiral as shown.

Additionally, the disposable cartridge could be used once or multiple times. In addition, the features of the Disposable Cartridge could be incorporated into a reusable system. This system would also then include a way of cleaning itself between individual measurements.

Other methods for measuring NO gas concentration in the measurement chamber also could be utilized, including (1) a spectrophotometric method, (2) a photo-colorimetric method, or (3) a chemiluminescence method.

One or more aspects and features of the present invention include: (1) a disposable cartridge that contains all of the non-gaseous fluid components; (2) NO blood measurement using an electrochemical gas sensor; (3) a disposable cartridge in which a sample is combined with a carrier gas, in which photolysis is performed on the sample, and in which any non-gaseous components from the sample are filtered-out; (4) a cartridge construction that is compact thus allowing for easy insertion and removal for disposal; (5) a completely closed NO extraction method which includes mixing of fluid with gas carrier, radiation to drive NO cleavage, outgassing of NO and separation from fluid/solids sample all within a closed system; and (6) pre-pressurization of such a closed system.

It is believed that one or more advantages of one or more embodiments of the present invention include: (1) Keeping all non-gaseous components of a fluid sample especially blood in the disposable cartridge reduces or eliminates the need to clean the Analysis Instrument thus making the device easier to maintain; (2) electrochemical gas sensors are smaller, less expensive and easier to maintain than other sensing methods such as fluorescent spectroscopy and chemiluminescence. (in addition, by measuring NO in gas form, this method is less complex and thus more reliable than the previously disclosed method where electrochemical fluid NO sensors were used); (3) a compact Disposable Cartridge design enables the entire test to be automated since all functions are performed together (this makes the device easier to use than previous devices and will require less maintenance); and (4) having a closed system which greatly enhances the ability to measure extremely low concentrations (ppb) (pre-pressurization further enhances this).

Still yet additional apparatus and methods for detecting nitric oxide in a fluid are disclosed in the invention disclosures forms of the attached Appendix, which is incorporated by reference herein and which forms part of the disclosure of embodiments of the present invention.

In view of the foregoing, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶16, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

What is provisionally claimed is:

1. A method for measuring a dissolved gas in a fluid comprising:
   liberating the dissolved gas from the fluid within a reaction chamber configured to receive electromagnetic radiation;
   capturing the liberated gas in a carrier gas in a sample degassing chamber fluidly connected to the reaction chamber for receiving the liberated gas; and
   measuring the dissolved gas concentration within a measurement chamber fluidly connected to the sample degassing chamber using an electrochemical sensor.

2. The method of claim 1, wherein the dissolved gas is nitric oxide.

3. The method of claim 1, wherein liberating the dissolved gas from the fluid includes:
   freeing the gas from its molecular bonds using electromagnetic radiation; and
   outgassing the dissolved gas from the fluid.

4. The method of claim 3, wherein using electromagnetic radiation includes using a light emitting diode.

5. The method of claim 3, wherein the outgassing includes heat vaporization.

6. The method of claim 1, wherein capturing the liberated gas includes capturing in an environment closed from ambient atmosphere.

7. An apparatus for measuring nitric oxide in a fluid, comprising:
   a disposable component for containing liquid or solid residue from a fluid sample containing entrained nitric oxide and configured to liberate nitric oxide gas from the fluid sample within a reaction chamber configured to receive electromagnetic radiation; and
   a reusable instrument component including a pump, a valve, a nitric oxide sensor, a control, and a user interface;
   wherein the disposable component is configured to connect to the reusable instrument for supplying liberated nitric oxide gas to a measurement chamber having a nitric oxide sensor.

8. The apparatus of claim 7, wherein the disposable component is configured for a single use.

9. The apparatus of claim 7, wherein the means for liberating nitric oxide gas from the fluid includes a means for outgassing the nitric oxide gas from the fluid sample within a sample degassing chamber fluidly connected to the reaction chamber to receive freed nitric oxide gas.

10. The apparatus of claim 7, wherein the control includes a microprocessor.

11. The apparatus of claim 7, wherein the nitric oxide sensor is an electrochemical sensor.

12. The apparatus of claim 7, wherein the apparatus includes a means for capturing the nitric oxide gas.

13. The apparatus of claim 12, wherein the means for capturing the nitric oxide containing gas is closed to ambient atmosphere.

14. The apparatus of claim 7, wherein the reusable instrument component includes the electromagnetic radiation source.

15. The apparatus of claim 14, wherein the electromagnetic radiation source is a light emitting diode.

16. The apparatus of claim 7, wherein the disposable component includes a means for containing the liquid and solid components of the fluid sample.

17. The apparatus of claim 16, wherein the means for containing the liquid and solid components of the fluid sample is a gas permeable membrane.

18. An apparatus for measuring nitric oxide in a fluid sample, comprising:
 a gas pump for supplying a carrier gas flow from a carrier gas reservoir;
 a valve selectively controlling the carrier gas flow from the carrier gas reservoir;
 a cartridge comprising:
  a sample chamber for receiving the fluid sample,
  a reaction chamber fluidly connected to the sample chamber to receive the fluid sample and configured to receive electromagnetic radiation from an electromagnetic radiation source to free NO gas from the fluid sample, and
  a sample degassing chamber fluidly connected to the reaction chamber to receive the fluid sample with freed NO gas and configured to receive thermal energy from a heater to drive outgassing of fluid through heat vaporization to outgas NO gas,
  wherein the sample chamber is configured to receive the carrier gas to move the fluid sample from the sample chamber into the reaction chamber and into the sample degassing chamber; and
 a measurement chamber fluidly connected to the sample degassing chamber for receiving the outgassed NO gas.

* * * * *